United States Patent [19]
Wainer et al.

[11] Patent Number: 5,807,926
[45] Date of Patent: Sep. 15, 1998

[54] IMMOBILIZED COFACTOR-DEPENDENT ENZYMES

[75] Inventors: Irving W. Wainer, Westmount, Canada; Vivian Sotolongo, Miami, Fla.; Daphne Wahnon, Montreal, Canada; Dean Johnson, Graz, Austria

[73] Assignee: McGill University, Montreal, Canada

[21] Appl. No.: 729,489

[22] Filed: Oct. 11, 1996

[51] Int. Cl.⁶ .............................. C12N 9/04; C12N 11/00; C12N 11/02; C12N 11/18

[52] U.S. Cl. ........................ 525/54.1; 435/189; 435/190; 435/193; 435/195; 435/233

[58] Field of Search ........................... 525/54.1; 435/189, 435/190, 193, 195, 233

[56] References Cited

U.S. PATENT DOCUMENTS

| | | |
|---|---|---|
| 4,006,059 | 2/1977 | Butler . |
| 4,221,869 | 9/1980 | Vandecasteele et al. ................ 435/117 |
| 4,525,454 | 6/1985 | Rozzell .................................. 435/106 |
| 4,931,498 | 6/1990 | Pidgeon . |
| 5,192,687 | 3/1993 | Bourdillon et al. .................... 435/280 |

FOREIGN PATENT DOCUMENTS

| | | |
|---|---|---|
| 0008656 | 3/1980 | European Pat. Off. . |
| 0186365 | 7/1986 | European Pat. Off. . |
| 0596490 | 5/1994 | European Pat. Off. . |
| 0645453 | 3/1995 | European Pat. Off. . |
| 34 32 220 | 3/1986 | Germany . |

OTHER PUBLICATIONS

Bradshaw, C.W. et al, "Enzymatic Synthesis of (R) and (S) 1-deuterohexanol" Applied Biochemistry and Biotechnology, vol. 33, No. 1, Apr. 1992, pp. 15–24, XP002053169.

Miyawaki, O., et al, "Experimental Investigation of Continuous NAD recycling by Conjugated Enzymes . . ." Journal of Chemical Engineering of Japan, vol. 15, No. 3, Jun. 1982, pp. 224–228.

Campbell, J. et al. "The Recycling of NAD+ (free and immobilized) with Semipermeable . . . Biochemical and Biophysical Research Communications, vol. 69, No. 2, 1976, pp. 562–569.

Haslegrave, J.A. et al, "Enzymes in Organic Synthesis. 25. Heterocyclic Ketones as . . . Journal of the American Chemical Society, vol. 104, 1982, pp. 4666–4671.

*Primary Examiner*—Nathan M. Nutter
*Attorney, Agent, or Firm*—Bachman & LaPointe, P.C.

[57] ABSTRACT

An oxido-reducto synthesis is carried out in a liquid medium with enzymatic transformation of a substrate with an oxido-reducto cofactor dependent enzyme in the presence of a cofactor for the transformation; the enzyme is immobilized by a support which is stationarily disposed in a flow path along which a liquid medium containing the substrate flows in contact with the support.

19 Claims, 4 Drawing Sheets

IMMOBILIZED COFACTOR-DEPENDENT ENZYMES

BACKGROUND OF THE INVENTION i) Field of the Invention

This invention relates to an oxido-reducto synthesis in which a substrate is enzymatically transformed by an immobilized cofactor dependent enzyme in the presence of a cofactor for the enzyme, more especially the invention is concerned with such a synthesis in which the substrate is racemic or prochiral and a product stream from the synthesis is chromatographically separated to provide pure product enantiomers.

ii) Description of Prior Art

Enzymatic transformations are extensively used in the synthesis of chiral chemicals and a wide variety of enzymes are used in these processes. Two key classes of enzymes employed in enantioselective syntheses are hydrolases and reductases. Hydrolytic enzymes, such as the lipases, have been extensively studied and are routinely used in research laboratories and in the chemical industry. The application of reductases to chiral synthesis has not been as extensively investigated or employed. This is due in part to the availability and stability of these enzymes as well as the fact that they require the use of cofactors such as NADH.

SUMMARY OF THE INVENTION

It is an object of this invention to provide a reduction synthesis employing an immobilized cofactor enzyme for the reduction, in the presence of a cofactor for the enzyme.

It is another object of this invention to provide an oxidation synthesis employing an immobilized cofactor enzyme for the oxidation, in the presence of a cofactor for the enzyme.

It is a further object of this invention to provide syntheses as aforementioned, in which the substrate is racemic or prochiral, and pure enantiomers are chromatographically separated from a product stream of the syntheses.

It is a particular object of the invention to provide syntheses as aforementioned which provide enantiomer selectively.

In accordance with the invention there is provided in an oxido-reducto synthesis in which a substrate, in a liquid medium, is enzymatically transformed with an oxido-reducto cofactor dependent enzyme in the presence of a cofactor for the enzyme in the enzymatic transformation, the improvement in which the enzyme is immobilized by a support, stationarily disposed in a flow path and said liquid medium containing said substrate flows along said flow path in contact with said support.

DETAILED DESCRIPTION OF INVENTION

The invention employs cofactor dependent reductases as enzymes in immobilized enzyme systems. The immobilized enzyme system is suitably supported as a stationary phase in an elongate column through which the substrate to be transformed by the enzyme flows as a substrate stream in a liquid medium, especially an aqueous medium. The substrate stream may flow through the column under pressure and for this purpose a column and related equipment employed in high pressure liquid chromatography may be utilized.

The flowing substrate stream contacts the stationary phase comprising the immobilized enzyme during flow through the column for the chemical reaction between the substrate and the enzyme. The cofactor for the enzyme must also be present for the chemical reaction to proceed.

The cofactor is typically included in the substrate stream and the substrate stream is continuously or continually recycled through the column to attain a desired level of transformation of the substrate.

Since the cofactor becomes depleted in the course of the reaction by conversion to a transformed state, it is appropriate to include in the substrate stream chemical reagents for the regeneration of the cofactor from the transformed state.

Typically the substrate stream may flow through the column at a flow rate of 0.05 ml/min to 2 ml/min preferably 0.1 ml/min to 1 ml/min, for a period of 0.5 to 50 hours, typically 18 to 48 hours at a temperature of from ambient to 40° C., typically at ambient temperature.

Additionally, it has been found that after continuous or continued recycling of a substrate stream containing the cofactor through the column containing the immobilized substrate, with concurrent regeneration of depleted cofactor in the stream, the cofactor may be omitted from the substrate stream and enzymatic activity is maintained. It is thought that the cofactor also becomes entrapped by the support forming an immobilized enzyme/cofactor complex, the cofactor being regenerated in situ by the chemical reagent in the stream.

i) Synthesis

The synthesis is an oxido-reducto synthesis, which in this specification refers to oxidation or reduction of a substrate with a cofactor dependent enzyme in the presence of the cofactor.

By way of example, the synthesis may be employed in the reduction of ketones to alcohols, or the oxidation of alcohols to ketones.

The syntheses of the invention may be employed with achiral, prochiral or racemic substrates.

The cofactor is the source of hydrogen for the reduction reaction, and the sink for hydrogen in the oxidation reaction.

In especially preferred embodiments, the synthesis employing the immobilized enzyme, when applied to a racemic or prochiral substrate is found to exhibit enantiomer selectivity, whereby one enantiomer of the racemic substrate is preferentially reduced or oxidized to produce a product stream richer in one enantiomer product than the other. This facilitates recovery by chromatographic separation of the enantiomer which forms the major product in the product stream, whereby the enantiomer product can be recovered in high purity.

The syntheses of the invention have the advantage in that the catalytic action of the enzyme provides ease of reaction under mild conditions; furthermore, easy separation of reaction products as well as prolonged use of the enzyme reactor is provided.

Suitable cofactor dependent enzymes for use in the invention include alcohol dehydrogenases, for example, horse liver alcohol dehydrogenase (HLADH) and Thermoanerobium brockii alcohol dehydrogenase (TBADH) which enantiospecifically reduce racemic and prochiral ketones to chiral alcohols. The cofactor for these dehydrogenases is NADH, the reduced form of β-nicotinamide adenine dinucleotide. HLADH and TBADH also enantioselectively oxidize achiral, chiral, prochiral and racemic alcohols to ketones and can be used to produce enantiomerically pure ketones. This oxidation is linked to the reduction of $NAD^+$, the oxidized form of β-nicotinamide adenine dinucleotide, to NADH.

Consequently, the immobilized cofactor dependent dehydrogenases can be employed in both oxidative and reductive syntheses.

The alcohol dehydrogenases such as HLADH and TBADH are suitable in cofactor dependent reduction of aldehydes, as well as in the reduction of acyclic and cyclic racemic or prochiral ketones. The alcohol dehydrogenases such as HLADH and TBADH are also suitable in cofactor dependent oxidation of primary and secondary alcohols, and for synthesis of chiral lactones by oxidation of diols, enantioselective oxidation of bicyclic alcohols, oxidation of prochiral diols and meso-diols.

The cofactor for the alcohol dehydrogenase is suitably NAD(P)H. In this regard, TBADH requires an NADPH cofactor, while HLADH requires NADH cofactor. Other cofactor dependent enzymes which can be utilized with this method include glutamate dehydrogenase {EC 1.1.1.6}, glycerol dehydrogenase {EC 1.1.1.6}, galactose oxidase {EC 1.1.3.9}, L-lactate dehydrogenase, L- and D-α-hydroxyisocaproate hehydrogenase and D-mandelate dehydrogenase.

ii) Immobilization

The cofactor dependent enzymes are immobilized by a support in a manner such that they do not lose their enzyme activity.

In particular, the enzyme may be non-covalently immobilized by hydrophobically entrapping it so that the enzyme is stationary relative to the flowing aqueous substrate stream, but at the same time the enzyme is conformationally mobile relative to the support. By this it is meant that the enzyme has a relatively fixed position but is mobile in such fixed position and is able to rotate about its fixed position to assume a conformation accessible to the cofactor and the substrate, to facilitate the chemical reaction.

One suitable immobilization support comprises inert particulate material, for example, silica particles, each particle having a plurality of membranous elements chemically affixed thereto so as to form the physical appearance of a fuzz on the particles. The enzyme being hydrophobic, preferentially locates itself between hydrophobic portions of the membrane elements, rather than migrating into the flowing aqueous stream.

An especially preferred class of support for the non-covalent immobilization of the enzyme, in accordance with the invention is described in U.S. Pat. Nos. 4,927,879 and 4,931,498, the teachings of which are incorporated herein by reference.

Typical immobilized membrane structures are illustrated schematically in FIGS. 2(a), 2(b), 3(a) and 3(c) of the aforementioned incorporated herein, U.S. Pat. No. 4,931,498.

In general, these immobilized membrane structures comprise a mechanically stable particulate support structure, more especially having physical dimensions appropriate for use in a chromatographic system, with an artificial membrane on the surface of the support structure. The membrane structures are, more especially, amphiphilic compounds having a hydrophilic headgroup portion and a hydrophobic portion. The amphiphilic compounds are oriented on the support structure so that the hydrophilic headgroup portion is outermost or remote from the support structure with the hydrophobic portion being between the support structure and the hydrophilic headgroup portion.

The free spaces or voids between adjacent hydrophobic portions of the membrane structure define zones in which an enzyme preferentially locates itself relative to an aqueous phase in contact with the membrane structures.

The hydrophobic portions of the membrane structure may be covalently bonded to the support structure or may hydrophobically interact with a hydrophobic surface of the support structure.

The membrane structures mimic the structural and physio-chemical characteristics of natural biological membranes. Suitable amphiphilic compounds for forming the membrane structures are the phospholipids.

Covalent bonding of the membrane structures to the support structures is generally preferred, as being more stable.

Suitable particulate support structures may be formed from, for example, silica, alumina, titania, or from resins having the necessary physical integrity. The particulate structures may typically have a particle size of 5 to 100 microns, preferably 5 to 50 microns, in diameter. Silica particles bearing covalently bound propylamine groups may be mentioned as an especially suitable class of support structure for covalent bonding to the membrane structures.

In general, the covalent bonding of the amphiphilic compounds to the support structures, particularly by way of surface functional groups on the support structures, is accomplished by a radiation-induced cross-linking reaction or by nucleophilic or condensation-type chemical reaction involving formation of, for example, ester, ether or amide bonds.

The aforementioned structures are of the so called Immobilized Artificial Membrane (IAM) type, which emulate the lipid environment of biological membranes by associating lipids with, for example, silica particles, for example, by covalent bonding or by hydrophobic interaction with a hydrophobic surface of the particle. One such support comprises monolayers of the amphiphilic membrane lipid molecules covalently bonded to aminoalkyl silica particles, for example, aminopropylsilica particles, through an amide linkage to the lipid alkyl chain. One particular support is marketed as IAM.PC by Regis Technologies Inc. and employs the lipid phosphatidyl choline (PC). The silica particles typically have a diameter of about 12 $\mu$m and have pores or voids defined by the membranes of about 300 Å in which the enzyme is entrapped.

The particulate support and the immobilized or hydrophobically entrapped enzyme is suitably employed as a bed in an elongate column, for example, an HPLC column. The substrate stream flows through the voids between adjacent particles and between the particles and the internal wall of the column, these voids forming part of the flow path of the substrate stream.

The invention is not, however, confined to the aforementioned non-covalent immobilization by hydrophobic entrappment, and in particular non-covalent or covalent immobilization by supports including inorganic and synthetic polymer supports is feasible provided that the enzyme activity is not lost in the immobilization. Examples of non-covalent immobilization of enzymes such as alcohol dehydrogenases include: physical adsorption on alumina, hexadecyl silica, polyaminomethyl styrene, silica or protein modified silica; or entrappment in collagen or polyacrylamide membranes. Examples of covalent immobilization of enzymes such as alcohol dehydrogenases include immobilization via tresylate.

iii) Chromatographic Purification

The flow path of the synthesis, along which the substrate stream flows may conveniently be connected on-line to a chromatographic separation system for example a high pressure liquid chromatography (HPLC) column containing a chiral stationary phase.

During recycling of the substrate stream through the bed of immobilized enzyme, the substrate stream is progressively converted to a product stream. This product stream may flow directly to the HPLC column for separation of the product enantiomers from unreacted substrate, and recovery of the individual enantiomers in high purity.

The process may also be operated with a continuous bleeding-off of a portion of the substrate stream during recycling through the bed of immobilized enzyme, and feeding of the bled-off portion through the HPLC column for separation of the product enantiomers and recycling of enantiomers of the substrate separated in the HPLC column. In this case, if only one of the product enantiomers is desired as reaction product, then the substrate enantiomer for this product alone may be recycled to the flow path through the bed of immobilized enzyme.

DESCRIPTION OF PREFERRED EMBODIMENT WITH REFERENCE TO DRAWINGS

Figure 3:
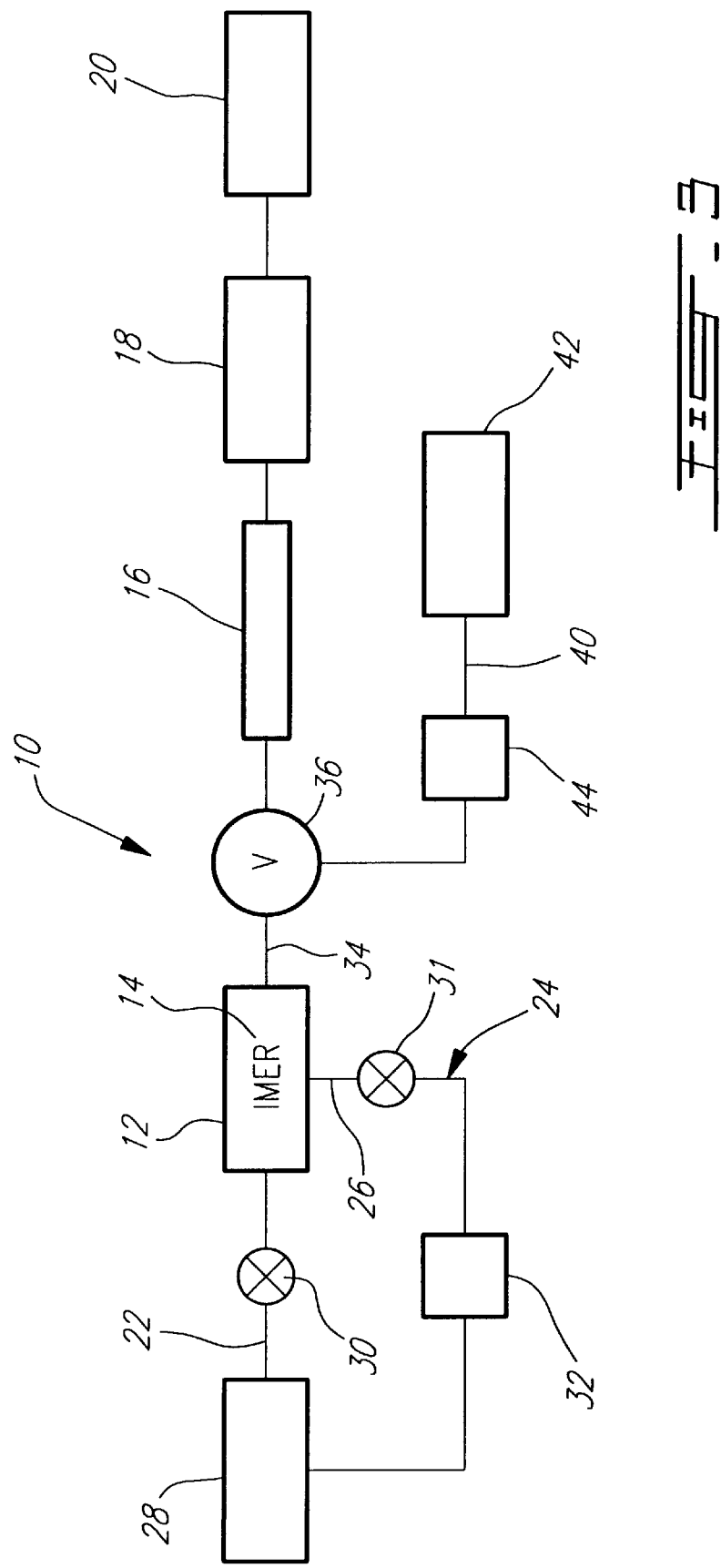
FIG. 3 is a schematic representation of a system for carrying out the synthesis of the invention, in conjunction with chromatographic separation of the enantiomers.

With further reference to FIG. 3 a system 10 for synthesis and recovery of pure enantiomers comprises a column 12 having immobilized enzyme 14, a high pressure liquid chromatography column 16, a detector 18 and an integrator 20.

A feed line 22 and a recycle line 24 define with column 12, a flow path 26 for a substrate solution. A pump 28 forces a flow of substrate stream under pressure in feed line 22 to column 12, a valve 30 controls flow in line 22.

A reservoir 32 in recycle line 24 provides a source of chemicals for regenerating the spent cofactor in the recycling substrate stream, and a source of supplemental substrate and cofactor line; 24 includes a valve 31.

Line 34 having a switching valve 36 connects column 12 and column 16; line 40 connects a pump 42 and valve 36; and reservoir 44 provides a source of eluent for column 16.

In operation, a substrate stream, for example, a stream containing a racemic or prochiral ketone, is pumped by pump 28 along feed line 22 to column 12. The substrate stream thus flows along flow path 26 defined by line 22, column 12 and recycle line 24. In column 12, flow path 26 is defined by voids between a particulate support which hydrophobically entraps the enzyme, and between the particles and the internal well of column 12. The substrate stream which at least initially contains cofactor for the enzyme contacts the immobilized enzyme 14 during its flow through column 12 whereby enzymatic transformation of the racemic or prochiral substrate occurs. The stream exiting column 12 by line 24 thus contains unreacted racemic or prochiral ketone and product enantiomer. This stream is recycled repeatedly along flow path 26, through column 12, until a desired level of enzymatic transformation of the racemic or prochiral ketone is achieved, and the stream is rich in product enantiomer. During this synthesis, switching valve 36 is closed and valves 30 and 31 are open.

When a desired enzymatic transformation is achieved, valve 31 is closed and switching valve 36 is opened for flow from column 12 to column 16. Pump 28 then forces the recycled stream through column 12 into line 34 and then to column 16, where the product enantiomers and unreacted substrate are absorbed. Switching valve 36 is then adjusted to permit flow of eluent from reservoir 44 under pressure from pump 42, into column 16 where chromatographic separation of unreacted ketone of the substrate and the product enantiomer occurs; the individual chromatographically separated components of the eluent are detected in detector 18 and determined in integrator 20.

EXAMPLE 1 a. Chemicals

Crystalline horse liver alcohol dehydrogenase {HLADH; EC 1.1.1.1}, β-nicotinamide adenine dinucleotide, reduced form (NADH) and oxidized form (NADH$^+$), glucose-6-phosphate dehydrogenase (Type XXIII: From Leuconostoc mesenteroides) and glucose-6-phosphate monosodium salt were obtained from Sigma Chemical Co (St. Louis, Mo., USA); magnesium chloride hexahydrate was obtained from ICN Biochemicals (Cleveland, Ohio, USA); sodium phosphate monobasic and dibasic were obtained from Fisher Scientific (Pittsburgh, Pa., USA); glycine, cyclohexanol, 2-cyclohexen-1-ol and benzyl alcohol were obtained from Aldrich Chemical Company (Milwaukeee, Wis., USA); all other chemicals were of the highest purity commercially available.

An IAM PC (12 $\mu$m, 300 Å) non-endcapped chromatographic support and the chromatographic column packed with IAM.PC (13 mm×4.1 mm, 12 $\mu$m, 300 Å) were obtained from Regis Technologies Inc. (Morton Grove, Ill., USA).

A racemic mixture of (R,S)-2-phenyltetrahydropyran-4-one {(R,S)-1} and the corresponding alcohols trans-(2R,4R; 2S,4S)-2-phenyltetrahydropyran-4-ol {(SS)-2, (RR)-5} and cis-(2R,4S; 2S,4R)-2-phenyltetrahydropyran-4-ol {(R,S)-3, (S,R)-4} shown below were prepared and identified by the procedures described hereinbelow.

b. Chromatographic System

Chromatographic experiments were performed with three modular HPLC systems. System A consisted of a Spectra Flow 400 chromatographic pump (ABI Analytical, Ramsey, N.Y., USA) a Rheodyne 7125 injector with a 20 $\mu$l sample loop (Rheodyne, Cotati, Calif., USA), and HLADH immobilized within the IAM.PC column {IAM-HLADH-IMER}.

System B consisted of a Spectra Flow 400 chromatographic pump, a HPLC column containing a chiral stationary phase (CSP) based upon p-methylphenylcarbamate derivatized cellulose (Chiralcel (trademark) OJR-CSP, Chiral Technologies Inc., Exton, Pa., USA), an ABI Spectra 100 UV-Vis detector set at λ=254 nm and a Data Jet integrator (Spectra-Physics, San Jose, Calif., USA).

Systems A and B could be used independently, or the eluent from system A could be directed onto system B through a Rheodyne 7000 switching valve.

System C consisted of a Spectra Flow 400 chromatographic pump, a HPLC column containing a HPLC-CSP based upon cellulose-3,5-dimethylphenylcarbamate (Chiralcel (trademark) OD-H, Chiral Technologies Inc.), an ABI Spectra 100 UV-Vis detector set at $\mu=254$ nm and a Data Jet integrator (Spectra-Physics).

c. Chromatographic Conditions

The mobile phase on System A consisted of aqueous solution of sodium phosphate buffer [0.05M, pH 7] and the flow rate was 0.1 ml/min. The mobile phase on System B consisted of sodium phosphate buffer [0.05M, pH 7]:acetonitrile (80:20, v/v) and the flow rate was 1.0 ml/min. The mobile phase on System C was hexane:2-propanol (97:3, v/v) and the flow rate was 1 ml/min. All of the chromatographic experiments were carried out at ambient temperature. All solutions were prepared using deionized water and filtered through 0.22 μm Millipore GVWP 047 filters (Millipore, Bedford, Mass., USA)

d. Immobilization of HLADH

The HLADH was immobilized on both the IAM.PC packing material and the IAM-HPLC column using the following procedures:

1. IAM-HLADH: 6 mg HLADH was dissolved in 6 ml sodium phosphate buffer [0.05M, pH 7] {Initial Solution} and IAM support (38 mg) was added. The mixture was gently shaken at ambient temperature for 3 h, filtered, the solid phase washed four times with 5 ml portions of phosphate buffer [0.05M, pH 7] and the washing combined with the Initial Solution{Final Solution}.

2. IAM-HLADH-IMER: 5 mg HLADH was dissolved in 15 ml phosphate buffer [0.05M, pH 7] and the solution was continuously circulated for 3 h through a 13 mm×4.1 mm I.D HPLC column containing IAM.PC stationary phase. The IAM-HLADH-IMER was washed with phosphate buffer [0.05M, pH 7] until a stable baseline was obtained and the washing were combined with the Initial Solution {Final Solution}.

3. Determination of Immobilized Enzyme: The amount of enzyme immobilized on the support was calculated from the difference in the amount of protein contained in the Initial Solution {determined before contact with the IAM.PC support} and the Final Solution. The protein concentrations were determined using a Bio-Rad Protein Assay (Bio-Rad Laboratories Ltd, Mississauga, ON, Canada).

4. Results of the enzyme Immobilization: Loose material (IAM-HLADH): 1.5 mg HLADH/38 mg IAM support HPLC column (IAM-HLADH-IMER): 415 μg HLADH/13 mm column e. Reductive Enzymatic Activity of the IAM-HLADH The enzymatic activity of the IAM-HLADH was determined by measuring the extent of the reduction of (R,S)-1. The 1 ml incubation solution contained the following reagents: NADH [1.1 mM], glucose-6-phosphate monosodium salt [16 mM], magnesium chloride hexahydrate [3 mM], glucose-6-phosphate dehydrogenase [5 U] and sodium phosphate buffer [0.05M, pH 7]. The reaction was initiated by the addition to the incubation solution of a suspension of the IAM-HLADH (100 μg of protein) and the substrate (1.41 mg, 8 μmol) in ethanol (100 μl). The resulting mixture was stirred at room temperature for 18 h, 24 h and 48 h.

The results of the incubations were assessed in the following manner: The incubation mixture was centrifuged and an aliquot (100 μl) of the supernatant was taken and diluted with water (400 μl); solid sodium chloride was added to the solution until saturation; diethyl ether (2.5 ml) was added and the resulting mixture vortexed for 2 min, centrifuged (2000 g, 10 min) and the organic phase collected, dried over anhydrous sodium sulfate and evaporated to dryness under a stream of nitrogen in a water bath at 20° C. The resulting residue was resuspended in the mobile phase for System B and analyzed on System B.

f. Reductive Enzymatic Activity of the IAM-HLADH-IMER

When the IAM-HLADH-IMER was used the incubation solution (1 ml) contained: NADH [0.11 mM], glucose-6-phosphate monosodium salt [1.6 mM], magnesium chloride hexahydrate [0.3 mM], glucose-6-phosphate dehydrogenase [2 U], (R,S)-1 [200 μg, 1.14 μmol] in ethanol [100 μl] and sodium phosphate buffer [0.05M, pH 7]. The solution was recirculated through the IAM-HLADH-IMER {System A} at 0.1 ml/min for 3 h and 18 h.

System A was then connected on-line to System B through the switching valve and the eluent (3.4 ml) from System A {which contained unreacted substrate and products} was directed to the OJR-CSP {System B} for stereochemical resolution and quantitation.

g. Influence of [E]/[S] Ratios on the Reductive Enzymatic Activities Free-HLADH and IAM-HLADH.

The influence of changes in the [E]/[S] ratio (enzyme concentration/substrate concentration) within the range $2.2\times10^{-6}$–$2.2\times10^{-2}$ was evaluated using the free-HLADH and the IAM-HLADH. The ketone (R,S)-1 [1 mg, 5.68 μmol], the free-HLADH and the IAM-HLADH [1 μg–1000 μg, $1.25\times10^{-5}$–$1.25\times10^{-2}$ μmol] were used. The reactions were performed following the IAM-HLADH above mentioned procedure. The chiral separation and quantitation were carried out using System C.

h. Oxidative Enzymatic Activity of the IAM-HLADH

The oxidative enzymatic activity of the IAM-HLADH was determined by monitoring the increase in absorbance at 340 nm due to the formation of NADH. Stock solutions of alcohol substrates [0.12M] were prepared in dioxane or glycine buffer [0.20M pH 9] and $NAD^+$ stock solutions [6.00 mM] were prepared in glycine buffer [0.20M pH 9]. Reaction mixtures (3 μl) were prepared by combining 100 ml $NAD^+$, 10 ml of substrate and 2890 μl of glycine buffer [0.20M pH 9]. The resulting solutions were 0.20 mM in NAD+ and 0.40 mM in substrate. Enzymatic reactions were initiated by the addition of 6 mg of IAM-HLADH. Blanks for the reactions containing all components except substrate were run simultaneously.

i. Enzymatic Oxidative Reactions using the IAM-HLADH-IMER

Prior to circulating the reaction mixture the reactor was washed with water, 10 min at a flow rate of 0.3 ml/min, followed by glycine buffer [0.20M, pH 9], 15 min at a flow rate of 0.3 ml/min. A 3 ml sample of 0.20 mM $NAD^+$, and 0.40 mM cyclohexanol in glycine buffer [0.20M, pH 9] was prepared. A blank sample containing all components except the substrate was also prepared.

Reaction mixtures were prepared by combining 100 ml of stock $NAD^+$ and 10 μl of cyclohexanol stock solution with 2890 μl of glycine buffer [0.2M, pH 9]. The resulting solutions were 0.20 mM in $NAD^+$ and 0.40 mM in cyclohexanol. The mixture was circulated through the IAM-HLADH-IMER. The activity of the IAM-HLADH-IMER was determined by monitoring the increase in absorbance at 340 nm due to the formation of NADH. Aliquots (800 ml) were removed from the reaction periodically, and recombined immediately after measuring the UV absorbance.

EXAMPLE 2 a. Reductive Enzymatic Activity of the IAM-HLADH

1. General Experimental Procedures

Figure 1:
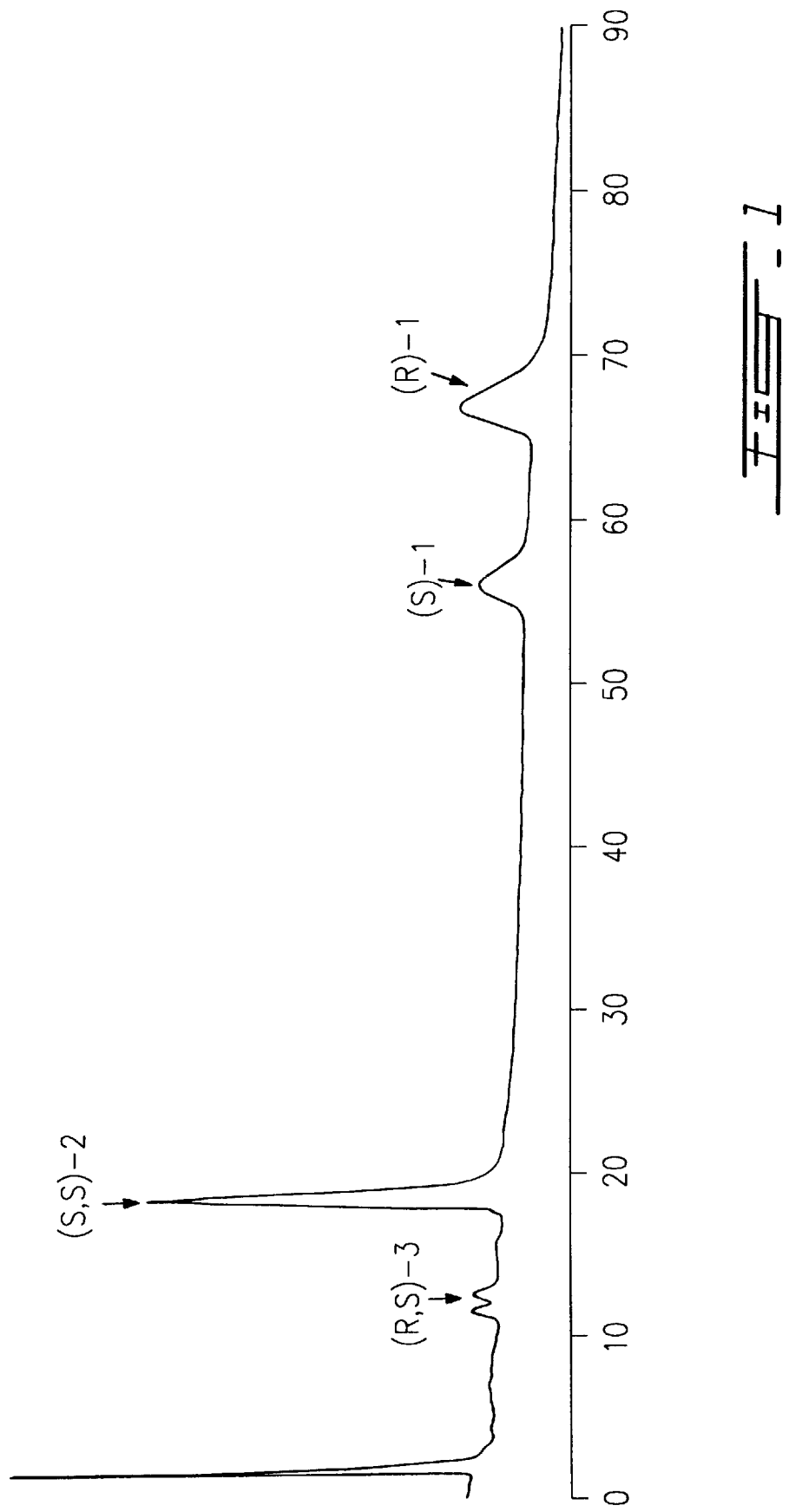
FIG. 1 is a chromatogram for a product stream produced by the enzymatic reduction of a racemic ketone in accordance with the invention, after a 24 hour reaction period.
Figure 2:
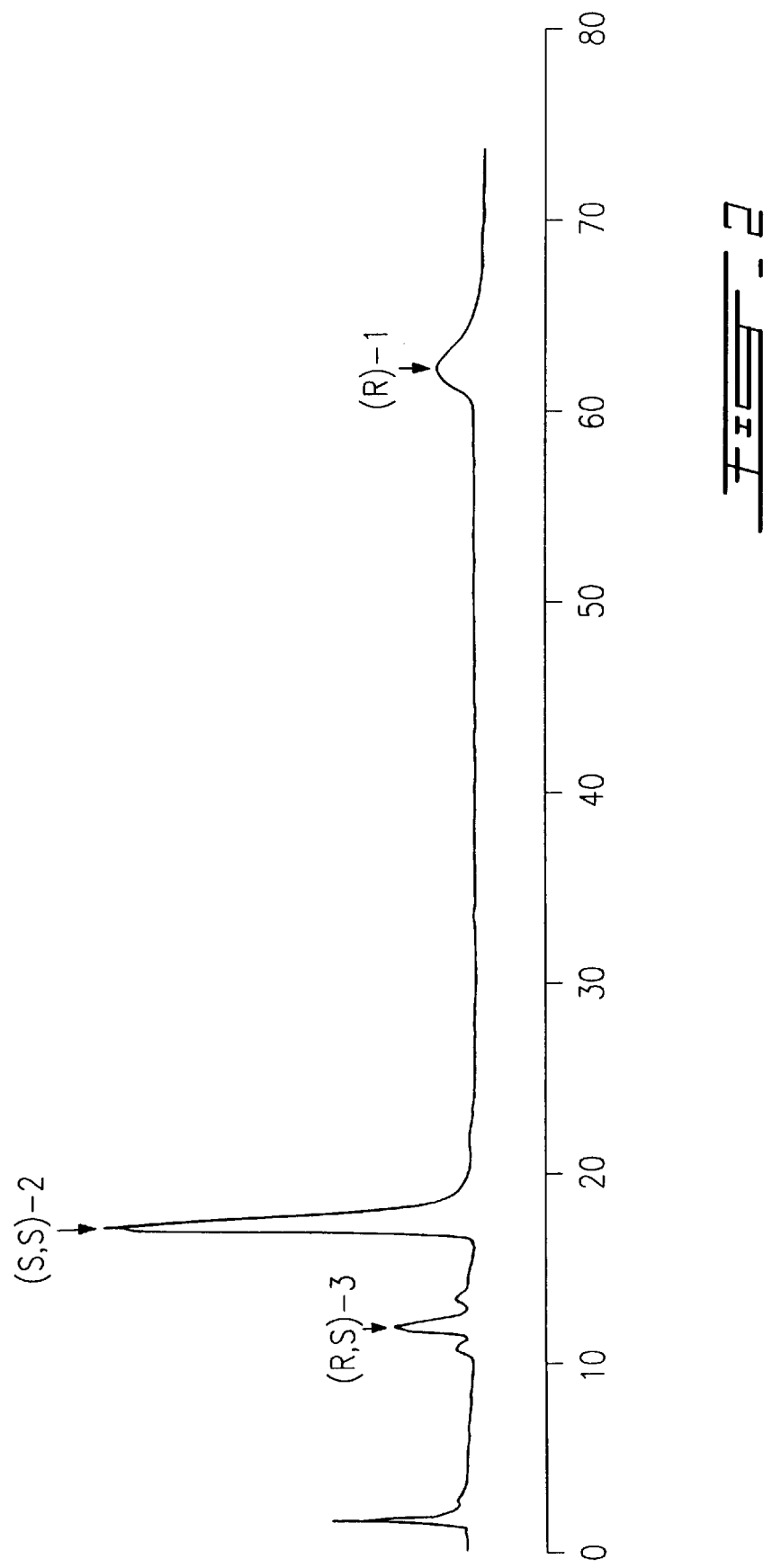
FIG. 2 is a chromatogram for the same reaction as FIG. 1, but for a 36 hour reaction period.

The effect of reaction time and enzyme/substrate ratio on the enzymatic activity and enantioselectivity of the IAM- HLADH as the loose packing material in Example 1 was investigated by following the reduction of (R,S)-1. The course of the reaction was followed by chromatographic analysis of the reaction mixture on System B {the OJR-CSP}. The chromatograms from the reaction mixtures contained peaks corresponding to cis-(2R,4S)-2-phenyl-tetrahydropyran-4-ol {(R,S)-3, at a relative retention, k, of 4.8}, trans-(2S,4S)-2-phenyl-tetrahydropyran-4-ol {(S,S)-2, k=7.6}, (S)-1 {k=24.6} and (R)-1 {k=29.6}, c.f. FIGS. 1 and 2. These results indicate that the immobilized HLADH retained its catalytic activity.

2. Effect of Reaction Time on the Extent and Enantioselectivity of the IAM-HLADH The effect of the reaction time on the extent and enantioselectivity of the IAM-HLADH catalyzed reduction of (R,S)-1 was investigated using 18 h, 24 h and 48 h reactions, and is summarized in Table 1 below.

TABLE 1

Extent of the reduction of (R,S)-1 on the IAM-HLADH as a function of time

| Reaction time | Percent Reduced (R)-1 | (S)-1 and (R)-1 (S)-1 |
|---|---|---|
| 18 h | 4 | 56 |
| 24 h | 6 | 82 |
| 48 h | 16 | 100 |

After 18 h, the IAM-HLADH enantioselectivity reduced the substrate to produce predominately (S,S)-2 {56% conversion of (S)-1} while (R,S)-3 was only a minor product {4% conversion of (R)-1}; a 14:1 preference for reduction of (S)-1. The relative enantioselectivity, i.e. 14:1 preference for (S)-1, was constant through 24 h while the extent of conversion rose to 82% for (S)-1 and 6% for (R)-1. At 48 h, 100% of (S)-1 and 16% of (R)-1 had been reduced and the relative enantioselectivity has fallen to 6:1. Representative chromatograms from 24 h and 48 h incubations are presented in FIGS. 1 and 2, respectively. These chromatograms demonstrate that the resulting alcohols were optically pure.

3. Influence of [E]/[S] Ratios on the Reductive Enzymatic Activities of Free-HLADH and IAM-HLADH The influence of the [E]/[S] ratio on the extent and enantioselectivity of HLADH catalyzed reductions was investigated using the free enzyme and the IAM-HLADH. The experiments were carried out at constant ambient temperature and time {18 h} with a constant (RS)-1 concentration {5.68 µmol} while varying the amount of enzyme. The results are summarized in Table 2 below.

TABLE 2

Influence of the [E]/[R] ratio on the free-HLADH and IAM-HLADH catalyzed reduction of (R,S)-1. Reaction carried out for 18 h.

| | Percent (R)-1 and (S)-1 Reduced Free | | | |
|---|---|---|---|---|
| | IAM-HLADH | | HLADH | |
| [E]/[S] ratio | (R)-1 | (S)-1 | (R)-1 | (S)-1 |
| $2.2 \times 10^{-6}$ | 2 | 22 | 0 | 3 |
| $2.2 \times 10^{-5}$ | 48 | 97 | 0 | 9 |
| $1.1 \times 10^{-4}$ | 55 | 100 | 17 | 46 |
| $2.2 \times 10^{-4}$ | 82 | 100 | 28 | 79 |
| $2.2 \times 10^{-3}$ | 100 | 100 | 35 | 100 |

For the free HLADH, an [E]/[S] ratio of $1.1 \times 10^{-4}$ was necessary to obtain a 100% conversion of (S)-1 while a 20-fold higher enzyme concentration was required to produce this result with IAM-HLADH {$2.2 \times 10^{-3}$}. However, the relative enantioselectivity was consistently better for the IAM-HLADH as compared to the free enzyme. At the optimum [E]/[S] ratios for (S)-1 conversion, i.e. $1.1 \times 10^{-4}$ for HLADH, $2.2 \times 10^{-3}$ for IAM-HLADH, the relative percent conversions of (S)-1:(R)-1 were 1.8 and 2.9, respectively. The source of this difference is not readily identifiable. However, it is conceivable that the immobilization of the enzyme in the interstitial cavities of the IAM support alters either the accessibility of the active site and the conformational structure of the enzyme or both of these components.

b. The Reductive Enzymatic Activity of the IAM-HLADH-IMER

1. Regeneration of NADH in the IAM-HLADH-IMER

The HLADH catalyzed reductions require the presence of the cofactor NADH. This cofactor is utilized in stoichiometric amounts and an economic utilization of HLADH requires using catalytic amounts of NADH together with an auxiliary system for regeneration of this cofactor. In order to accomplish this in the IMER-based chromatographic system, an enzymatic method was used for the regeneration of NADH. This approach employs the oxidation of glucose-6-phosphate to 6-phosphogluconolactone which hydrolyzes to 6-phosphogluconate by glucose-6-phosphate dehydrogenase (G-6-PDH) from Leuconostoc mesenteroide to produce the reduced cofactor. The enzyme is readily available, inexpensive and accepts both $NAD^+$ and $NADP^+$. The regenerating substrate is available, cheap, stable and the glucose-6-phosphate/G-6-PDH system has a high reducing potential.

The regeneration system was connected in-line before the switching valve (FIG. 3). The mobile phase was directed through the regeneration system during the course of the enzymatic reactions. In order to facilitate the interactions between enzyme, substrate and cofactor, a flow rate of 0.1 ml/min was used during the recirculation. Using this system, the enzymatic reactions were carried out for up to 48 h.

2. (R,S)-1 on the IAM-HLADH-IMER

The substrate, (R,S)-1 was injected onto the IMER and the mobile phase was recirculated through the regeneration system for 18 h. At the end of the reaction, the regeneration system was disconnected from the IMER and the enzymatic reactor was connected on-line to the OJR-CSP (FIG. 3). The mobile phase containing the products of the reaction were directed to the analytical column where they were resolved and quantified on the chiral stationary phase.

The results for 7 consecutive reactions on the same IAM-HLADH-IMER are presented in Table 3 below.

TABLE 3

Extent of the reduction of (R,S)-1 on the IAM-HLADH-IMER and the enantioselectivity of the reaction as a function of time with or without NADH

| | WITH NADH % Reduction | | WITHOUT NADH % Reduction | |
|---|---|---|---|---|
| REACTION # | (S)-1 | (R)-1 | (S)-1 | (R)-1 |
| 1 | 20 | 4 | 0 | 0 |
| 2 | 30 | 10 | 6 | 2 |
| 3 | 50 | 18 | 5 | 3 |
| 6 | 37 | 17 | 28 | 13 |
| 7 | 47 | 15 | 51 | 17 |

The data indicates that the HLADH had retained its enzymatic activity and reduced (R,S)-1 to (S,S)-2 and (R,S)

-3; the alcohols were chirally pure. During the first two reaction cycles, the activity of the enzyme, as indicated by the reduction of (S)-1, appeared to be diminished relative to the free IAM-HLADH. However, by the third cycle, comparable levels of (S)-1 reduction were achieved, 50% IAM-HLADH-IMER vs 56% IAM-HLADH. While the percent reduction of (S)-1 eventually reached parity, the conversion of (R)-1 was always greater on the IAM-HLADH-IMER than the IAM-HLADH. On the IAM-HLADH-IMER, the relative enantioselectivity of the conversion plateaued at (S)-1:(R)-1≈3:1 while after an 18 h incubation, the same ratio derived from the IAM-HLADH was 14.1.

After the creation of an IAM-HLADH-IMER, injection of the substrate into a system which contained the regeneration solution but no NADH, resulted in no observable reduction of the substrate. This is to be expected, since NADH is a necessary component of the enzymatic transformation. However, after a single reductive cycle in which NADH was circulated through the IAM-HLADH-IMER, removal of the NADH from the mobile phase still resulted in residual enzymatic activity, Table 3. After 7 reactive cycles, comparable enzymatic activity was observed with or without NADH in the mobile phase, Table 3.

The data indicates that an immobilized enzyme/cofactor complex has been created and that the necessary NADH is regenerated in situ. Therefore, it is no longer necessary to add NADH to the reaction mixture, reducing the expense involved in the production of the chiral alcohols. The creation of the emzyme/cofactor complex may also explain the observed increase in the reduction of (R)-1 relative to the free HLADH.

c. Oxidative Enzymatic Activity of IAM-HLADH

The oxidations of cyclohexanol, 1-cyclohexen-2-ol and benzyl alcohol were observed with the IAM-HLADH as loose packing material. A change in absorbance over time was observed for these substrates using stock solution [0.12M] in dioxane.

Dioxane had a marked effect on the extent of the oxidation reaction with the IAM-HLADH. When the substrate was dissolved in glycine buffer [0.20M, pH 9] instead of dioxane, product formation increased by greater than 100%.

The results from the oxidation of cyclohexanol with free HLADH in the presence and absence of dioxane produced only a small inhibitory effect. The observed loss of enzymatic activity on the IAM-HLADH produced by the presence of a relatively small (10 μl) amount of dioxane is most likely due to solvent induced changes in the stationary phase. The dioxane either interferes with the ability of the substrates to reach the immobilized enzyme or alters the structure of the instial spaces leading to a conformational change of the HLADH.

The IAM-HLADH was subjected to multiple cycles of cyclohexanol oxidation. Only a slight loss of activity (10% as measured by total change in absorbance) was observed for the IAM-HLADH over the course of five oxidative cycles in five days. After each use, the IAM-HLADH was stored in glycine buffer [0.20M, pH 9].

Oxidation of cyclohexanol by HLADH immobilized on a prepacked IAM-HPLC was also observed. The activity of the IAM-HLADH-IMER was determined by periodic UV absorbance measurements. A control experiment was run initially on a newly prepared IMER in which all the reaction components except the cyclohexanol substrate were circulated through the IAM-HLADH-IMER. After the control experiment, the oxidation of cyclohexanol was initiated using [0.4 mM] cyclohexanol in glycine buffer [0.20M, pH 9]. The change in absorbance over time for the control and cyclohexanol oxidation is presented in Table 4 below.

TABLE 4

The change in uv absorbance over time as a measure of oxidative transformation of cyclohexanol on an IAM-HLADH-IMER; where Blank = control experiment, Cyclohexanol = addition of [0.12M] cyclohexanol to the IAM-HLADH-IMER.

| Time (mins | Absorbance Blank | Absorbance Cyclohexanol |
|---|---|---|
| 15 | −0.007 | 0.063 |
| 30 | 0.049 | 0.105 |
| 45 | 0.066 | 0.126 |
| 105 | 0.077 | 0.144 |
| 115 | 0.077 | 0.154 |
| 130 | 0.081 | 0.159 |
| 145 | 0.081 | 0.172 |

EXAMPLE 3

The racemic mixture of Example 1 and the procedures for identification were as follows:

EXPERIMENTAL

Chemicals

Benzaldehyde and 3-butenol were purchased from Aldrich (Milwaukee, Wis., USA). HPLC-grade hexane and 2-propanol were purchased from Anachemia (Montreal, Quebec, Canada). Horse liver alcohol dehydrogenase (E.C.1.1.1.1.) was purchased from Sigma Chemical Company (St. Louis, Mo., USA). All other chemicals were reagent grade and used as purchased. Chromatographic Apparatus and Conditions The chromatographic system consisted of a Spectroflow 400 solvent and delivery system (ABI Analytical, Ramsey, N.J., USA), a 7125 Rheodyne injector with a 20 μl sample loop (Cotati, Calif., USA), a 783 ABI programmable absorbance detector (ABI Analytical) set at λ=254 nm, and a Chrom-Jet integrator (Thermo Separations Products, San Francisco, Calif., USA).

The columns used were a nitrile guard column (5 μm, 75×4.6 mm I.D.; Regis Technologies, Inc., Morton Grove, Ill., USA), a 250×4.6 mm I.D. column containing a chiral stationary phase (CSP) based upon amylose tris(3,5-dimethylphenyl carbamate) coated as 10 μm silica-gel (Chiralpak AD-CSP; Chiral Technologies, Inc., Exton, Pa., USA) and a 250×4.6 mm I.D. column containing a CSP based upon cellulose tris(3,5-dimethylphenyl carbamate) coated on 5 μm silica (Chiralcel ODH-CSP; Chiral Technologies, Inc.). The column configurations were either the guard column/AD-CSP or guard column/ODH-CSP/AD-CSP.

The mobile phases consisted of mixtures of hexande:2-propanol, 99:1 (v/v) for the AD-CSP and 95:5 (v/v) for the ODH-CSP/AD-CSP system. The flow rate was 1.0 ml/min and the experiments were run at ambient temperature (22° C.). Synthesis of rac-trans-2-phenyltetrahydropyran-4-ol {rac-5} and rac-cis-2-phenyltetrahydropyran-4-ol-{rac-6}

Compounds of rac-5 and rac-6 were synthesized according to the method described by Hanschke, E. Zur Kenntnis der Prinsschen Reaktion III. Mitteil.: Über die Reaktion von Allylcarbinol mit Aldehyden und Ketonen. Chem. Ber. 88:1053–1061, 1955. In brief, sulfuric acid {400 μl; 80% [w/v]} was added to a cooled (0° C.) solution of 3-butenol {8.00 mmol} and benzaldehyde {4.00 mmol} and the solution was stirred for 16 h, during which time it was allowed to warm to room temperature. The mixture was poured onto crushed ice, neutralized by the addition of solid sodium bicarbonate and extracted with diethyl ether (3×70 ml). The organic phases were combined, dried over anhydrous sodium carbonate, filtered and concentrated in vacuo. The oily residue was resuspended in water {15 ml} and solid sodium sulfite was added to the point of saturation. The mixture was stirred at room temperature for 30 min, extracted with diethyl ether (3×70 ml). The organic phases were then combined, dried over anhydrous sodium sulfate, filtered and concentrated in vacuo. The products were purified by flash chromatography on Merck silica gel 60 using hexane: ethyl acetate, 7:3 (v/v) as the eluent. The alcohols were prepared in a vis/trans ratio of 17:1 as determined by HPLC analysis.

The products were analyzed by IR, $^1$H- and $^{13}$C-NMR (300 MHz) techniques. The spectral data obtained were consistent with the proposed structures. IR (CHCl$_3$): 2840, 2940 (O-H), 1070 (C-O) cm$^{-1}$; $^1$H-NMR (CDCl$_3$): 1.50–1.70 (m, 3H, C-5CH$_2$ and O-H), 1.93–2.23 (dq, J=15 Hz and 3 Hz, 1H, C3CH$_2$), 2.15–2.23 (dq, J=15 Hz and 3 Hz, 1H, C3CH$_2$), 3.52–3.63 (dt, J=12 Hz and 2.5 Hz, 1H, C2CH$_2$), 3.98–4.01 (m, 1 H, C4CH), 4.15–4.22 (ddd, 1H, J=12 Hz, 7.5 Hz and 2.5 Hz, C6CH$_2$), 4.27–4.36 (dd, 1H, J=12 Hz and 2.5 Hz, C6CH$_2$), 7.23–7.40 (m, 5 H, aryl hydrogens); $^{13}$C-NMR (CDCl$_3$): 35.56 (C5), 43.34 (C3), 63.88 (C6), 65.63 (C4), 75.96 (C2), 125.93, 127.69, 128.46, 139.39 (aryl carbons).

Synthesis of (R,S)-2-phenyltetrahydropyran-4-one {rac-4}

Compound (RS)-1 was prepared from rac-5 and rac-6 using the oxidation method outlined by Swern, D. et al., Oxidation of long-chain and related alcohols to carbonyls by dimethyl sulfoxide "activated" by oxalyl chloride. J. Org. Chem. 43:2480–2482, 1978. A reaction time of 30 min was employed and the crude workup residue was purified by flash chromatography on silica gel 60 using hexane:ethyl acetate, 85:15 (v/v) as the eluent.

The products were analyzed by IR, $^1$H- and $^{13}$C-NMR (300 MHz) techniques. The spectral data obtained were consistent with the proposed structures. IR (CHCl$_3$): 1730 (C=O), cm$^{-1}$; $^1$H-NMR (CDCl$_3$): 2.38–2.80 (m, 4 H, C-5CH$_2$ and C3CH$_2$), 3.79–3.90 (dt, J=16.5 Hz and 4.5 Hz, 1H, C2CH), 4.39–4.48 (ddd, 1H, J=10.5 Hz, 6.0 Hz and 2.5 Hz, C6CH$_2$), 4.61–4.68 (dd, 1H, J=10.5 Hz and 2.5 Hz, C6CH$_2$), 7.23–7.40 (m, 5H, aryl hydrogens); $^{13}$C-NMR (CDCl$_3$): 42.23 (C5), 50.01 (C3), 66.82 (C6), 79.33 (C2), 125.70, 128.22, 128.73, 140.70 (aryl carbons), 206.32 (C=O). Enzymatic reduction of rac-4 by horse liver alcohol dehydrogenase (HLADH)

(RS)-1 was reduced with HLADH following the procedure described by Haslegrave and Jones, Enzymes in organic synthesis. 25. Heterocyclic ketones as substrates of horse liver alcohol dehydrogenase. Highly stereoselective reductions of 2-substituted tetrahydropyran-4-ones. J. Am. Chem. Soc. 104:4666–4671, 1982. In short, the incubation mixture of 1 ml volume contained the following reagents (final concentration): NAD$^+$(1.1 mM), HLADH (100 ml of a 1 mg/ml stock solution, 100 mg), (R,S)-4 (1.41 mg, 8 mmol) in ethanol (100 ml) and potassium phosphate buffer [pH 7.0, 100 mM] (686 ml).

The incubations were sampled by removing a 100 ml aliquot which was diluted with 100 ml of water and sodium chloride was added to the point of saturation. Diethyl ether (250 ml) was added and the resulting mixture was vortexed for 2 min, followed by centrifugation at 2000 g for 10 min. The organic phase was collected and dried over anhydrous sodium sulfate. The diethyl ether was transferred to a clean tube, evaporated under a stream of nitrogen and the residue dissolved in 200 ml mobile phase and injected onto the chromatographic system.

Figure 4:
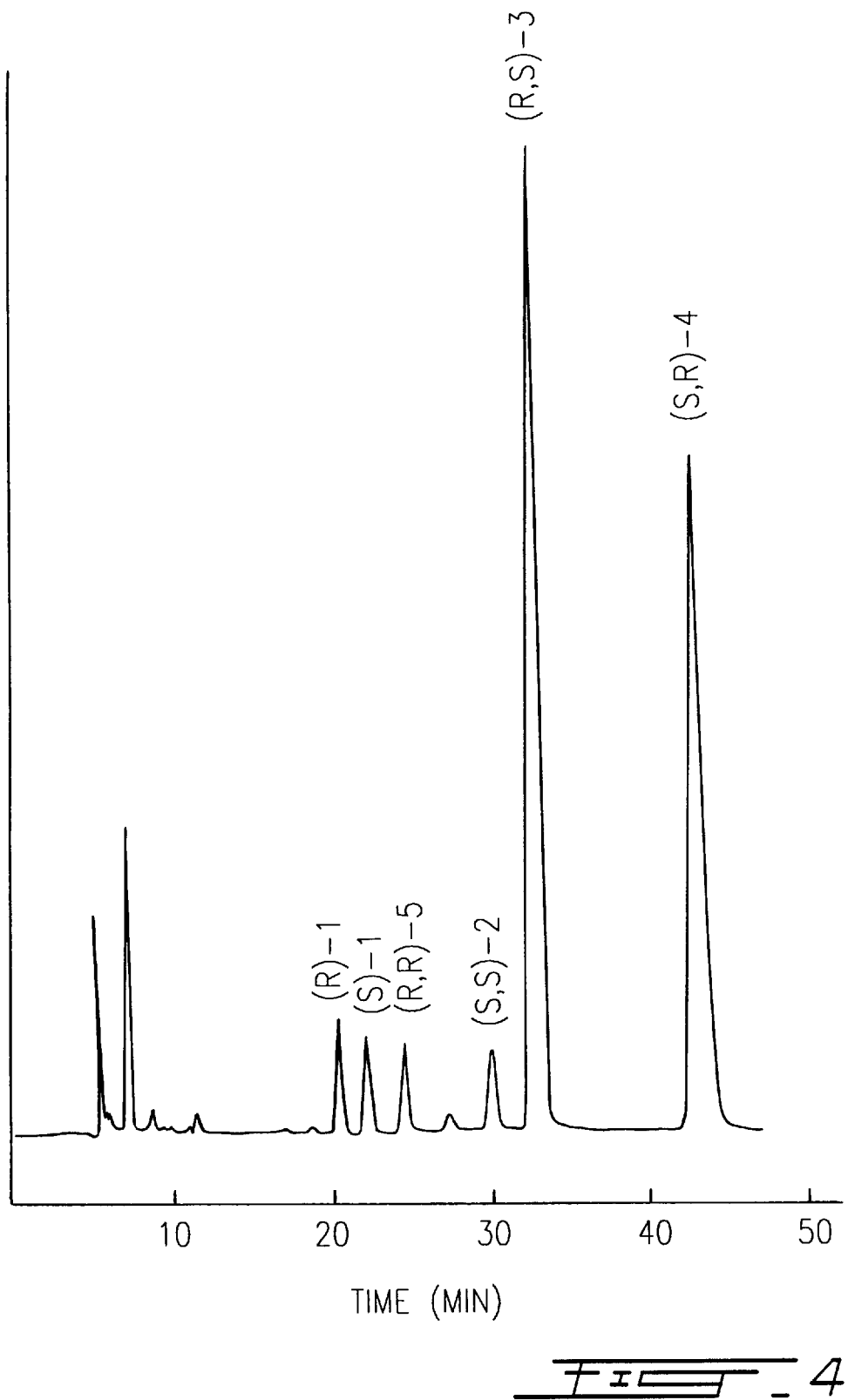
FIG. 4 is a chromatogram of a substrate and enantiomers of the substrate.

Enantioselective and Diastereoselective Resolution of Compounds 4, 5 and 6 on the Coupled OD-H-CSP/AD-CSP System The results from the chromatography of the Compounds on the OD-H-CSP/AD-CSP system are presented in Table 5 and FIG. 4. The peaks corresponding to (R)-1 and (S)-1 were identified by chromatography of the synthetic racemate and the peaks corresponding to the four enantiomers of racemic 2-phenyltetrahydropyran-4-ol (i.e. S,S-2; R,S-3; S,R-4 and R,R-5) were identified from the chromatography of the products from the sodium borohydride reduction of (RS)-1.

As illustrated in Table 6, the enantioselective separations of the ketones and alcohols could be achieved separately on the OD-H-CSP and AD-CSP. However, the complete diastereoselective and enantioselective separation of all the stereoisomers of the alcohols could not be achieved on the OD-H-CSP alone, or by in-line coupling of an achiral precolumn. While adequate enantioselective separations of the ketones and alcohols were not achieved on the AD-CSP, the three compounds were amply resolved from each other. The coupling of the two CSPs produced the desired complete enantioselective and diastereoselective resolutions. It did not matter which CSP was placed first in the series and the enantioselectivities were not additive.

The enantiomeric elution order for each of the components was determined by following the enzymatic reduction of (RS)-1 by horse liver alcohol dehydrogenase (HLADH). Haslegrave and Jones above have reported that during the initial 24 h of HLADH mediated reduction of (R,S)-1 only (S)-1 is reduced producing a single, enantiomerically pure product, (S,S)-2, and after 72 h (R)-1 is reduced to (R,S)-3. Thus, the relative retention times of four of the six compounds were established. The relative retention times of the remaining two compounds, (R,R)-5 and (S,R)-4 were established using the product from the initial synthesis of rac-5 and rac-6. The NMR spectra of the reaction mixture indicated that the cis:trans ratio {i.e. 6:5} of the products was 17:1 which is consistent with the previously reported results of Haselgrave and Jones above, from this synthesis. The chromatographic analyses of the reaction mixture and of the reaction mixture doped with the products from the 72 h enzymatic reduction resulted in the identification of the relative retentions of (R,R)-5 and (S,R)-4.

We claim:

1. In an oxido-reducto synthesis in which a substrate, in an aqueous medium, is enzymatically transformed with an oxido-reducto cofactor dependent enzyme in the presence of a cofactor for the enzyme in the enzymatic transformation, the improvement in which the enzyme is non-covalently, hydrophobically entrapped by a support comprising a particulate bed stationarily housed in an elongate column, a flow path extending along said column through voids between adjacent particles and between said particles and an internal wall of said column, said aqueous medium containing said substrate flows along said flow path in contact with said support, the non-covalent, hydrophobic entrapment of said enzyme being such that said enzyme is stationary relative to said flowing aqueous medium and conformationally mobile relative to said support.

2. A synthesis according to claim 1 in which said cofactor is in said flowing aqueous medium.

3. A synthesis according to claim 1 in which said flowing aqueous medium contains chemical reagents for regeneration of cofactor transformed in the synthesis.

4. A synthesis according to claim 1 in which said cofactor is non-covalently entrapped by said support such that the cofactor is stationary relative to said flowing aqueous medium in a conformationally mobile state accessible to said enzyme.

5. A synthesis according to claim 1 in which said support comprises membranous elements affixed to inert particles of said bed, and said enzyme is entrapped between the membranous elements.

6. A synthesis according to claim 1 which comprises reduction of a racemic or prochiral ketone to an alcohol, in which said enzyme is an alcohol dehydrogenase and said cofactor is reduced β-nicotinamide adenine dinucleotide, NADH.

7. A synthesis according to claim 1 in which said substrate is racemic or prochiral and including flowing enzymatically, transformed substrate from said flow path and chromatographically separating enantiomerically pure transformation products from the enzymatically transformed substrate.

8. A synthesis according to claim 7 in which the chromatographic separation is carried out in a high pressure chromatography column.

9. A process for producing pure enantiomers from an enzymatically transformable racemic or prochiral precursor of the enantiomers comprising:
   i) forming a stream of an enzymatically transformable racemic or prochiral precursor in an aqueous medium,
   ii) flowing said stream along a flow path and into contact with an oxido-reducto cofactor dependent enzyme entrapped in said flow path by a support comprising a particulate bed stationarily housed in an elongate column, said flow path extending along said column through voids between adjacent particles of said bed and between said bed and an internal wall of said column, said contact being in the presence of a cofactor for said enzyme, and enzymatically transforming said prochiral or racemic precursor to product enantiomers,
   said enzyme being non-covalently, hydrophobically entrapped by said support such that said enzyme is stationary relative to said flowing medium and conformationally mobile relative to said support,
   iii) removing a product stream containing said product enantiomers from said flow path, and
   iv) chromatographically separating said product enantiomers in said product stream to provide the pure enantiomers.

10. A process according to claim 9 in which the chromatographic separation is carried out in a high pressure liquid chromatography column.

11. A process according to claim 10 in which said racemic precursor is a racemic or prochiral ketone, said enzyme is an alcohol dehydrogenase and said cofactor is reduced β-nicotinamide adenine dinucleotide, NADH.

12. A process according to claim 11 in which said cofactor is a component of said stream in step i).

13. A process according to claim 10 in which said racemic or prochiral precursor is a racemic or prochiral alcohol, said enzyme is an alcohol dehydrogenase and said cofactor is oxidized β-nicotinamide adenine dinucleotide, $NAD^+$.

14. A synthesis according to claim 5 in which said particles comprise silica particles having a particle size of 5 to 100 microns in diameter.

15. A synthesis according to claim 4 in which said particles comprise silica particles having a particle size of 5 to 50 microns in diameter, said silica particles having membranous elements affixed thereto, and said enzyme being entrapped between the membranous elements.

16. A synthesis according to claim 8 in which said particles comprise silica particles having a particle size of 5 to 50 microns in diameter, said silica particles having membranous elements affixed thereto, and said enzyme being entrapped between the membranous elements.

17. A synthesis according to claim 5 wherein said aqueous medium flows along said flow path in contact with said support in said elongate column at a flow rate of 0.05 ml/min to 2 ml/min, the aqueous medium being recycled repeatedly through said elongate column to provide a contact time of 0.5 to 50 hours between said substrate, enzyme and cofactor.

18. A process according to claim 10 in which said flow path is defined by a feedline to said elongate column, said particulate bed in said column and a recycle line from said elongate column to said feedline and step ii) comprises flowing said stream repeatedly along said flow path at a flow rate of 0.1 ml/min to 1 ml/min for a period of 18 to 48 hours.

19. A process according to claim 18 including feeding chemical reagents for regeneration of cofactor transformed during formation of said product enantiomers into said recycle line.

* * * * *